United States Patent [19]

Eberhardt

[11] Patent Number: 5,176,153
[45] Date of Patent: Jan. 5, 1993

[54] HEART CHAMBER SIMULATOR WITH ELECTRONIC ACCELERATED HEART VALVE WEAR AND FATIGUE TEST APPARATUS AND METHOD

[76] Inventor: Allen C. Eberhardt, 7408 Wingfoot Dr., Raleigh, N.C. 27615

[21] Appl. No.: 608,660

[22] Filed: Nov. 2, 1990

[51] Int. Cl.⁵ .............................................. A61F 2/24
[52] U.S. Cl. .................................... 128/897; 623/2; 73/37
[58] Field of Search .............................. 128/897, 898; 600/16-17; 623/2, 3; 73/37, 46

[56] References Cited

U.S. PATENT DOCUMENTS

| | | | |
|---|---|---|---|
| 4,381,663 | 5/1983 | Swanson | 73/37 |
| 4,450,710 | 5/1984 | Nettekoven | 73/37 |
| 4,546,642 | 10/1985 | Swanson | 73/37 |

FOREIGN PATENT DOCUMENTS 0239723 10/1986 German Democratic Rep. ... 600/16
1577782 7/1990 U.S.S.R. ..................................... 623/2

Primary Examiner—Lee S. Cohen
Assistant Examiner—John P. Lacyk
Attorney, Agent, or Firm—Irving M. Freedman

[57] ABSTRACT

An accelerated wear and fatigue tester for replacement human heart valves includes a fluid which is caused to pulse the heart valve by a pressure generator utilizing a coil secured to a flexible diaphragm in contact with the fluid. The coil is subjected to a magnetic field and a signal selected from pulsed, sinusoidal, or random pulses and/or a DC offset, or a recorded signal from a human heart, such that the magnetic interaction selectively pulses the diaphragm and replacement heart valve to simulate heart action. A plurality of pressure generators with differing signals, including phase differences, may be provided to simulate arrhythmia in a heartbeat, and a library of recordings may be used as a database to predict irregularities in replacement heart valves.

35 Claims, 2 Drawing Sheets

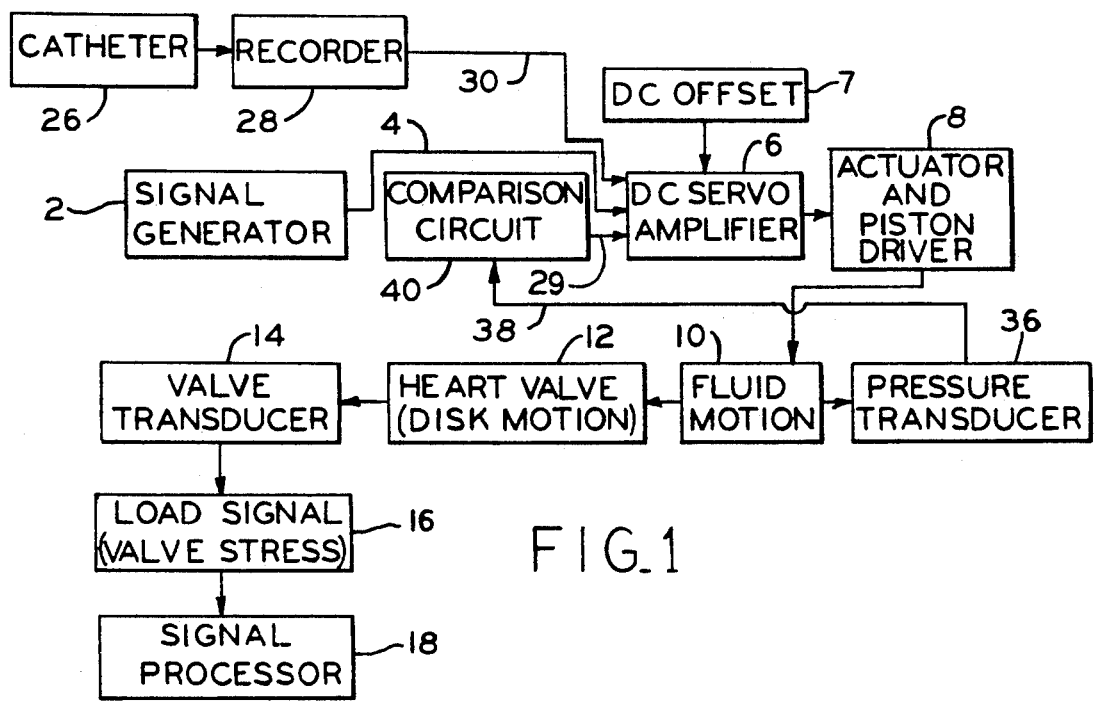
FIG_1
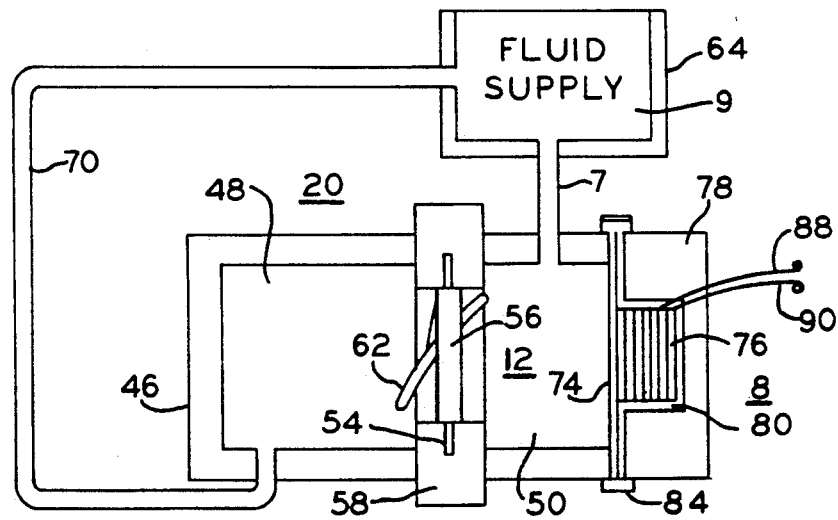
FIG_2
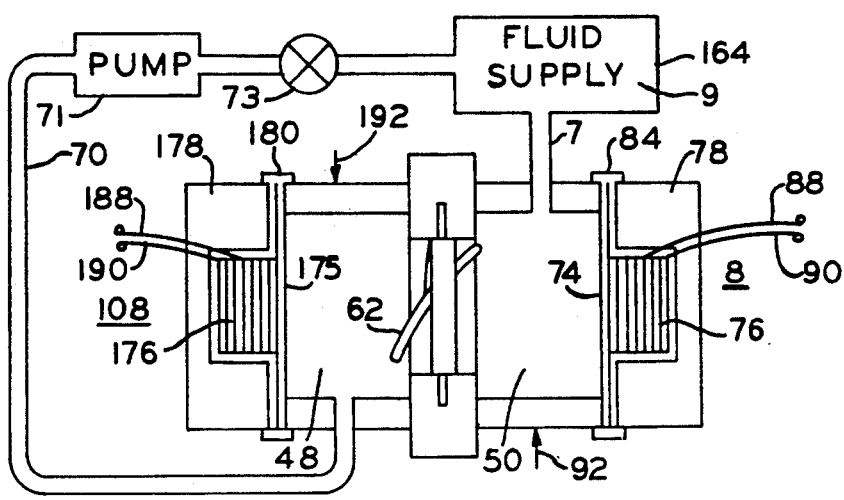
FIG_3

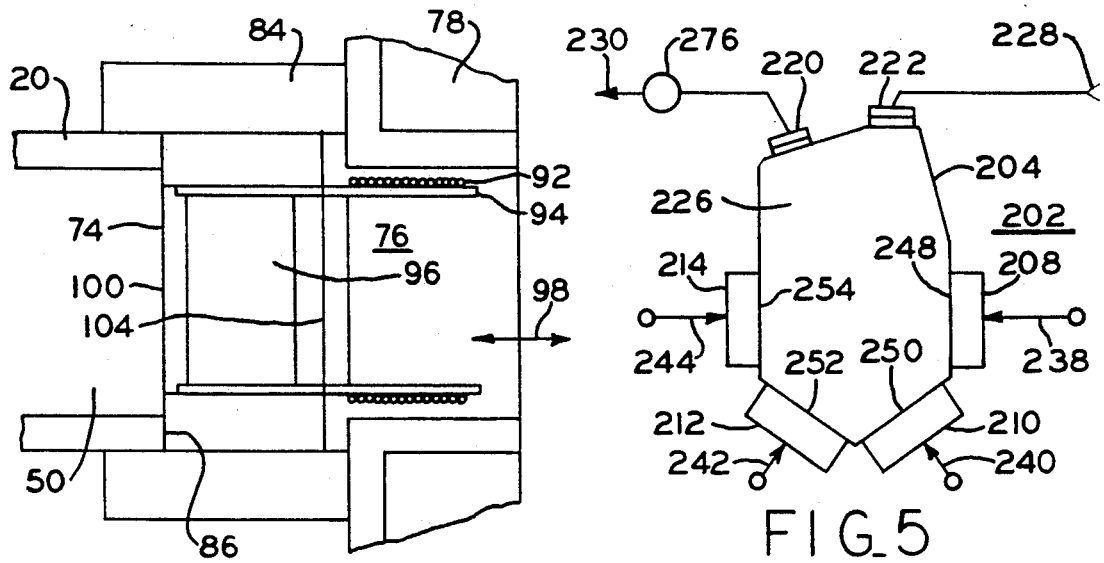
FIG_4
FIG_5
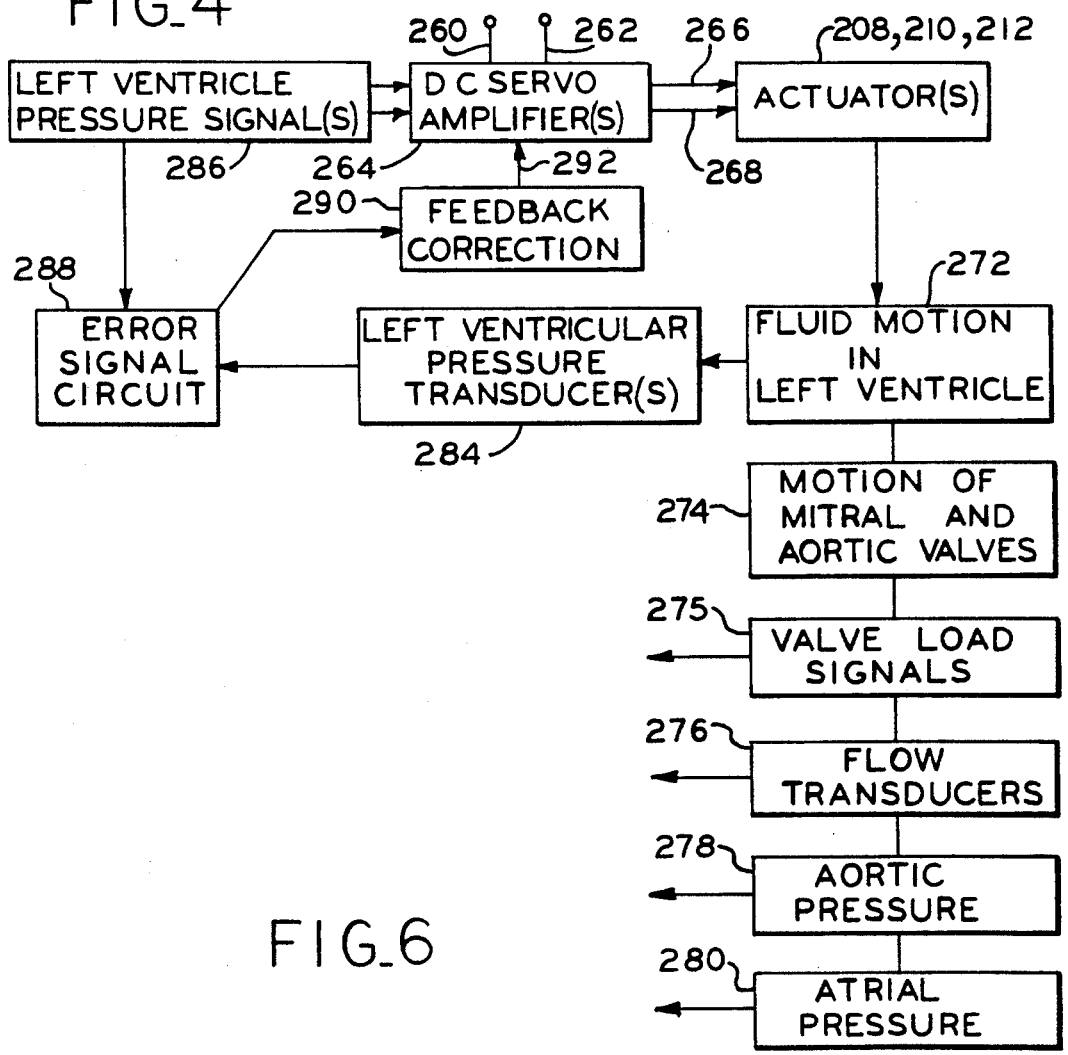
FIG_6

HEART CHAMBER SIMULATOR WITH ELECTRONIC ACCELERATED HEART VALVE WEAR AND FATIGUE TEST APPARATUS AND METHOD

BACKGROUND OF INVENTION

The present invention relates to a replacement heart valve simulator with an accelerated wear and fatigue tester, in which the rate and type of testing may be varied, and in which the suitability of replacement heart valves for particular humans may be evaluated.

Existing systems for testing heart valves for use as replacements in humans provide means to pulse fluids, such as water, through the replacement valve to test the operation and life of such valves in vitro. One method provides a control valving arrangement to provide an alternating air pressure and vacuum against a diaphragm exposed to the liquid, in order to move the diaphragm first in one direction and then the other direction against the liquid to cause the liquid to pulse the valve. Such arrangements have tended to buckle and distort the diaphragm, which have introduced anomalies into stress measurements which may be undertaken on the replacement valve being tested. In addition, various mechanical arrangements have been proposed and used to apply a pressure to the diaphragm using an eccentric and variable-stroke motor driven apparatus requiring complex linkage arrangements and drive systems. However, such arrangements have proved to be noisy, providing problems in the acoustical testing of the operation of the replacement heart valves. In addition, the various existing arrangements normally provide on-off or square wave pulsing, or a mechanical sinusoidal input signal provided through use of a crank and piston arrangement.

However, it is desirable to be able to selectively apply a variety of input signals in the testing of such valves, including pulsed, sinusoidal, triangular and random signals, to be able to control the phasing of multiple signals, and further including signals recorded from an actual heart, in order to more closely simulate or reproduce the fluid flow conditions which may be encountered in the operation of a human heart. In addition, it is desirable to be able to simulate an arrhythmic heart, and also to be able to accurately and directly control the pressure applied to the heart valve being tested so as to be able to provide a wide range of test pressures.

Still further, it is desirable and often necessary to be able to accelerate the testing of the replacement heart valves to accomplish necessary testing in available or reasonable time periods.

In addition, it is desirable to be able to predict potential irregularities in an implanted in vivo replacement heart valve by monitoring and comparing its operation with a response database compiled by recording the operation of in vitro replacement heart valves and noting operational characteristics prior to development of irregularities.

OBJECTS AND BRIEF SUMMARY OF INVENTION

It is an object of the present invention to provide a replacement heart valve simulator with an accelerated wear and fatigue tester for the heart valves.

It is another object of the present invention to provide a replacement heart valve simulator with an accelerated wear and fatigue tester which is actuated in response to a control signal selected from various signals, including those produced by a human heart.

It is yet another object of the present invention to provide a replacement heart valve simulator which is actuated in response to signals which can simulate an arrhythmia in a human heartbeat.

It is still another object of the present invention to provide a replacement heart valve simulator which is actuated in response to a plurality of signals, the magnitude and phases of which may be varied in order to simulate various abnormal conditions of operation of the human heart.

It is a further object of the present invention to provide a replacement heart valve simulator with an accelerated wear and fatigue tester for fluid valves used as replacements in the human heart which is quiet in operation in order to enable audio analysis and testing of the replacement heart valves.

It is a still further object of the present invention to provide a replacement heart valve simulator with an accelerated wear and fatigue tester for human heart replacement valves which provides direct control over the applied force and the magnitude of flow of the liquid used in such testing.

It is a yet further object of the present invention to provide a simulated heart in which to test the operation of replacement heart valves.

It is another object of the present invention to compile a database of recordings of the response and operation of in vitro replacement heart valves and compare it with in vivo response and operation in order to predict the development of possible irregularities, and the suitability of various replacement heart valves, for a particular human.

In accordance with one embodiment of the present invention, an accelerated wear and fatigue tester for fluid valves such as those used as replacements in the human heart is provided in which the heart valve assembly is mounted in a fluid system in which fluid is pumped by one or more pressure generators which apply a periodic pressure to the fluid to actuate the heart valve in response to the movement of a pulsed diaphragm in response to an input signal. An electromagnetic coil is secured to the diaphragm and positioned for movement within a magnetic field provided by a permanent magnet associated with the coil. The interaction of the electromagnetic field resulting from the input signal flow through the coil and the permanent magnet magnetic field results in movement of the coil and diaphragm in response to the input signal. The input signal provided by a signal generator may be selected from pulsed, sinusoidal or random signals, and may include a DC offset. The variable frequency of the input signal may be made much higher than the range of the normal heartbeat of the human heart in order to accelerate the test procedure.

In one embodiment of the present invention, a plurality of pulsed diaphragms are included in the fluid system and may be phased or actuated differently to simulate arrhythmia and other heart abnormalities. The replacement heart valve may be secured in place by a DACRON sewing ring of the type used in actual human heart valve replacements, and a closed loop pressure generating system may be provided to control the applied pressure and rate of fluid flow through the heart valve being tested. Also, a plurality of pulsed diaphragms may be arranged to simulate a human heart, and actual recordings of a human heart may be used as the input signal in the testing of replacement heart valves, or in the selection of a replacement heart valve for a particular individual.

BRIEF DESCRIPTION OF THE DRAWINGS

FIG. is a block diagram illustrating operation of the present invention;

FIG. 2 shows one embodiment of the pulsed pressure generating or pumping diaphragm or pressure duplicator used in FIG. 1; and FIG. 3 is an alternate embodiment of the pulsed diaphragm pressure duplicator used in FIG. illustrating the use of a plurality of pressure generating or pumping diaphragms.

FIG. 4 is an enlarged view of the diaphragm portion of FIGS. 2 and 3.

FIG. 5 shows a simulated left ventricle of a human heart using multiple pulsed diaphragm pressure duplicators of the type shown in FIGS. 2, 3 and 4.

FIG. 6 is a block diagram of a system including the simulated heart of FIG. 5.

DETAILED DESCRIPTION OF THE INVENTION

Referring to FIG. 1, the signal generator 2 selectively provides an input signal 4 which may be sinusoidal, square wave, triangular, random or pulsed. The signal 4 is fed through the comparison circuit 40 and the DC servoamplifier 6 where it is amplified and provided to the actuator and piston driver or pressure generator 8 to provide a pressure to a fluid 9 which varies in accordance with the signal provided to the DC servoamplifier or amplifier 6. The piston driver 8 includes a diaphragm in contact with fluid 9 producing fluid pressure and motion in response to the signal 4, which pressure and motion is provided through the fluid to the heart valve 12 resulting in actuation of the heart valve disk in response to the pulsing of the signal 4. A valve transducer 14 monitors the action of the heart valve disk providing a load or valve stress signal 16 which can be fed to a signal processor 18 to develop stress data relating to the operation of heart valve 12 for use as described in more detail below.

Alternatively, the input signal to the DC servoamplifier 6 may, instead of the in vitro signal 4 provided by signal generator 2, be an in vivo signal 30 developed from the recording of a heart patient, or a person with a normal heart, through use of a catheter 26 inserted into the person which provides a signal to the recorder 28, which is then used to provide the in vivo electronic signal 30 through comparison circuit 40 to the DC amplifier 6. A pressure transducer 36 may be provided in contact with the fluid motion 10 to develop a feedback signal 38 representing the actual pressure of the fluid applied to the heart valve 12. The feedback signal is fed to comparison circuit 40 where it is compared with a variable desired or reference pressure signal to develop an error signal 29 for application to DC amplifier 6 to provide closed loop operation to conform the actual pressure in the fluid 9 to the desired pressure.

The details of the construction of the actuator and piston driver 8 are shown in FIGS. 2, 3 and 4. Referring to FIGS. 2, 3 and 4, the actuator and piston driver 8 of the simulated heart chamber 20 is positioned within a closed, generally cylindrical, chamber 46 with the replacement heart valve assembly 12 mounted across the interior dividing the chamber into return portion 48 and supply portion 50. The DACRON fabric sewing ring 54 surrounding the generally circular frame 56 of the heart valve 12 is secured in the circumferential support 58. The sewing ring 54 is the ring normally used in implanting the heart valve 12 into a human and is thus also subjected to testing along with the heart valve. In a manner well known in the art, the heart valve assembly 12 includes an occluder valve or disk 62 which periodically rotates or pivots between open and closed positions in response to the fluid (or blood) pressure applied to it. This periodically connects the return portion 48 with the supply portion 50 of chamber 46. A source of fluid 9 is provided by the fluid supply 64 to the supply portion 50 of the chamber 46. A solution of 38% glycerol in water has been found to provide approximately the same viscosity and density as blood and is a preferred liquid for use in connection with the subject invention. The return portion 48 of the chamber 46 is connected by way of the fluid return line 70 to the fluid supply 64.

The actuator and piston driver 8 is positioned across the open end of the supply chamber 50 of the vessel 20 and includes a flexible diaphragm 74 across the inner end in contact with the fluid 9. The diaphragm 74 is fabricated from silastic. A coil 76 is attached in the central region of the flexible diaphragm 74. Surrounding the coil 76 is a permanent magnet 78 which is generally cylindrical in shape with a central opening closely conforming to the exterior of the coil 76 and forming a narrow air gap 80 between the coil and the permanent magnet. The permanent magnet 78 provides a magnetic field through the air gap 80 around the coil 76. The output signal from the DC servoamplifier 6 is connected to the coil 76 by flexible leads 88 and 90 which enable the provision of the desired signal, either the in vivo signal 30 or the selected signal 4.

FIG. 4 shows the details of the mounting of the diaphragm and associated moving coil. Referring to FIG. 4, the coil assembly 76 includes the coil 92 wound on the tubular aluminum frame 94. A nylon cylinder 96 is secured within the tubular aluminum frame 94 for movement therewith, and provides support and mass to the coil assembly 76. Movement of the coil assembly 76 is in the direction of the arrow 98; that is, back and forth against the flexible diaphragm 74 to which the coil assembly is secured. The coil assembly 76 moves in response to current flow through the coil 92, and the resultant electromagnetic field as described below.

The flexible diaphragm 74 is secured to the end rim 86 of the vessel 20 by a silastic sealer which is also used to seal the coil assembly 76 to the flexible diaphragm. To facilitate assembly and disassembly, a circular hole 100 is provided in the center of the flexible diaphragm 74 which, upon assembly, is sealed by the nylon cylinder, or plug, 96. A support diaphragm 104 of a general annular configuration is positioned around tubular aluminum frame 94 to support the coil assembly in the end region of the nylon cylinder 96 which is remote from the flexible diaphragm 74. The supporting diaphragm 104 is sealed around the periphery of the coil assembly 76 and provides support to the coil assembly while at the same time being flexible to enable movement of the coil assembly.

To further expand the flexibility in simulating in vivo operational conditions on the heart valve 12, a plurality of piston drivers such as 8 may be provided. One such arrangement is shown in FIG. 3. Referring to FIG. 3, it is seen that the end of the return portion or chamber 48 includes a second actuator and piston driver 108 which is essentially the mirror image of the actuator and piston driver 8 across the open end of the supply portion or chamber 50. It is possible to provide a different signal to the actuator and piston driver 108 than is provided to the actuator and piston driver 8. For example, the signal applied to the leads 188 and 190 of actuator and piston driver 108 can be different from, or alternatively could be the same but out of phase with, the signal applied to the leads 88 and 90 of the actuator and piston driver 8. This provides the possibility of actuating the heart valve 12 in an asymmetrical mode of operation to simulate irregularities and arrhythmia, and other heart abnormalities.

The signal provided to the coil 76 generates an electromagnetic field which interacts with the magnetic field produced by the permanent magnet 78 to cause axial displacement or movement 98 of the coil 76 in accordance with the direction and magnitude of the signal. Axial displacement of the coil 76 also displaces the attached diaphragm 74 in contact with fluid 9 providing a pressure signal on the fluid 9 which varies in accordance with the signal provided by the DC amplifier 6. The pulsed variable pressure signal applied through the fluid 9 actuates the pivoted occluder disk 62 of the heart valve 12 allowing fluid flow through the heart valve from the supply portion 50 to the return portion 48 of chamber 46. The reversal of direction of the pressure caused by a reversal of direction of movement of the coil 76 and/or the actuation of the coil 176 of piston driver 108 (see FIG. 3) results in a greater pressure in the return chamber 48 than in the supply chamber 50 pushing the pivoted occluder 62 back to the closed position. As a result, the pivoted occluder disk 62 pivots first clockwise to allow fluid flow from the supply chamber 50 to the return chamber 48 and then pivots counterclockwise to close the flow path. The frequency and movement of the pivoted disk 62 thus responds to the direction and pressure provided by the diaphragm 74 of piston driver 8 and/or the diaphragm 175 of piston driver 108 on the liquid 9 in response to the signals applied to the coils 76 and/or 176 of the piston drivers.

Since the heart valve system shown in FIG. 1 allows the selective provision of in vitro sinusoidal, triangular, square or random actuating pulses, or even in vivo signals, and further including a DC offset which may be provided to the DC servoamplifier 6 by the DC offset 7, the pressure signal applied to the heart valve 12 may be selectively tailored in shape, frequency, and magnitude. This enables the simulation of a variety of conditions and situations which may be encountered in the human body in order to enable testing of the heart valve 12 over a wide span of variables.

Still additional actuators and piston drivers could be provided. For example, an additional actuator and piston driver could be provided in the supply chamber 50 along the bottom surface indicated by arrow 92 in FIG. 3 and/or a still further additional actuator and piston driver could be provided to the return chamber 48 at the upper side indicated by the arrow 192. Thus, two or more actuator and piston drivers could be provided to enable the introduction of out of phase, and differing, signals to different actuators and piston drivers to further provide flexibility in simulating the pressure applied by a human heart to the heart valve 12. Phase differences can be selectively provided through the use of multiple signal generators 2 including phase shifting means or through the use of phase shifters in circuit with one or more of the actuators and piston drivers.

It is desirable to be able to test the effects of cavitation on a heart valve to determine what, if any, effect cavitation has on the operation of heart valves. Cavitation is the formation of a cavity or hole between the downstream surface of a moving body and a liquid normally in contact with it. In order to facilitate study of the operation and durability of the design of replacement heart valves in the presence of cavitation, the present invention may be readily converted to a closed system with controlled cavitation effects. Referring to FIG. 3, it is noted that the fluid supply 164 is in the form of a closed vessel, and a variable speed pump 71 is provided in combination with a valve 73, both of which are shown in the fluid return line 70, although they may be provided in the fluid supply line 7. Adjustment of the speed of the pump 71 and valve 73 enable control of the steady state or mean fluid pressure and flow. The pumping action provided by the actuator and piston drivers 8 and 108 is superimposed as an oscillation or variation of the pressure applied to, and flow through, the replacement heart valve 12. Through control of the variable speed pump 71 and valve 73, and control of the actuation of the piston drivers 8 and 108, the ability to control pressure and flow, and to vary and study the effects of cavitation on the replacement heart valve 12, is enhanced.

It is to be noted that accelerated testing and wear of heart valves by the various embodiments described above is possible by simply increasing the frequency of the signals provided to the DC servoamplifier 6 and in turn to the actuator and piston drivers, such as 8 and 108. This can be used to accelerate a wear, life, or other test on the heart valve 12. The human heartbeat is normally in the range of 50 to 200 cycles or beats per minute. The signal generator 2, for example, can provide signals at a frequency of up to 400 cycles per second, or much higher. The in vivo signals 30 can be provided, for example, by a variable speed tape player which can be speeded up to increase the frequency of the in vivo signals, or by computer digitization and analog reconstruction of the in vivo signals.

The valve transducer 14 (see FIG. 1) or other test instrumentation provided can be used to measure stress applied to the heart valve 12 and/or can include a microphone or audio-detector to sense and record the audible noise produced by the opening and closing of the pivoted disk 62 of the heart valve 12. By simulating an abnormality or arrhythmia condition in the signal applied to the actuators and piston drivers such as 8, it is possible to record the response signals (load signal 16) to study the response of the heart valve over a period of time to such input signals.

It is not only possible to test the heart valve 12 for proper operation and failure through a life test, but it is also possible to evaluate how the valve responds to different environments of heart pressure and different functioning or different input wave shapes. Acoustical and/or stress measurements obtained on a heart valve 12 in vitro can be analyzed and monitored to provide reference information, or an in vitro response database, which can be useful in analyzing acoustic and other responses and measurements obtained from an implanted in vivo heart valve. It may then be possible to correlate tests from the monitoring of an implanted in vivo heart valve with tests from an in vitro heart valve by comparing the implanted heart performance data with the in vitro response database. Such a comparison can be used to predict proper functioning of an implanted heart valve, or to predict the development of potential irregularities in the implanted valve. A library of test sounds, signals and resultant operation and reliability can be assembled to assist in identifying abnormal stress and/or potential irregularities or failures of heart valves. It might be possible, for example, to determine in vitro which sounds exhibited by replacement heart valves represent high stresses or potential irregularities and then look for these same sounds or signals from in vivo replacement heart valves in patients through use of a microphone, stethoscope, or other sensor.

In the testing of replacement heart valves, it is desirable to be able to simulate as closely as possible the operation of such valves in a human heart in order to test the response and durability of the replacement heart valves under various conditions of excitation and fluid flow. Such an arrangement is shown in FIG. 5.

Referring to FIG. 5, the simulated heart left ventricle 202 is shown, which includes a pair of human heart valves 220 and 222 attached to and providing controlled passage through the simulated heart chamber 204 and arranged to provide fluid flow into the simulated heart chamber through valve 222 as indicated by arrow 228, and fluid flow out of the simulated heart chamber through heart valve 220 as indicated by arrow 230. A plurality of heart valve actuators 208, 210, 212 and 214 are mounted in apertures in the simulated heart chamber 204 and are of the configuration shown by the heart valve actuator 8 in FIGS. 2, 3 and 4. The heart valve actuators 208, 210, 212 and 214 are mounted such that their diaphragms such as 74 (see FIG. 2) are in contact with the liquid within the simulated heart chamber 204, which may be conveniently fabricated of a transparent elastomer or of plastic. Signals 238, 240, 242 and 244 are provided to heart valve actuators and piston drivers 208, 210, 212 and 214, respectively, to actuate the diaphragms 248, 250, 252 and 254, respectively, in accordance with the input signals to each of the actuators and piston drivers. As discussed and described above, the input signals 238, 240, 242 and 244 may be selected from the group consisting of sinusoidal, triangular, square wave or random pulses, may include a DC offset, may be selectively phased, and may be a signal derived from the recording of an actual human heart. Through a combination of signal selection and signal phasing, the fluid pressure and fluid flow through the heart valves 220 and 222, and the actuation of the heart valves, may be tailored to simulate that experienced when such valves are implanted in vivo in a human heart.

A block diagram of a system incorporating the simulated left ventricle 202 is shown in FIG. 6. Referring to FIG. 6, the input signals 260 and 262 may selectively be of different phases and may comprise a plurality of different signals, although only two are shown, and may include the recorded signal of a human heart as discussed above. The input signals such as 260 and 262 are fed to the DC servoamplifier or amplifiers 264 which provide a plurality of signals, two of which, 266 and 268, are shown, applied to the heart valve actuators 208, 210, 212 and 214. The actuators 208, 210, 212 and 214 provide actuation of the diaphragms 248, 250, 252 and 254, respectively, to provide a movement and pressure against the liquid 226 within the simulated heart chamber 204, which produces a pumping action and liquid flow 228 in through heart valve 222, and the liquid flow 230 out through heart valve 220. Since the actuators 208, 210, 212 and 214 are energized through electronic signals, the frequency of the actuation may be controlled and/or varied, and may be accelerated above the normal frequency of a human heart to compress the desired number of cycles into a shortened test period.

As shown by FIG. 6, instrumentation may be applied to provide a plurality of indications and measurements of the response of the simulated left ventricle 202 to the simulated heartbeat provided by signals 260 and 262. This may include the measurement and recording of the action of the heart valves 220 and 222 through valve load signals 275 and also may, as desired or required, include flow measurements through the use of a flow transducer or flow meter 276, which may be positioned as shown in FIG. 5 in the liquid flow 230 line. In addition, pressure measurements may be taken of the aortic pressure and the atrial pressure through appropriately positioned pressure transducers 278 and 280 of the simulated left ventricle 202.

The pressure in the simulated left ventricle 202 may be measured by one or more pressure transducers 284, which can be used in a closed loop feedback system to maintain the pressure within the simulated left ventricle 202 at the desired pressure. Gain controls in the DC servoamplifiers 264 can also provide an adjustable control of the magnitude of the signals 266 and 268 provided to the actuators such as 208, 210, 212 and 214. The left ventricle desired pressure signals 286 are provided to the error signal or comparison circuit 288, which also receives the actual pressure signals from the left ventricular pressure transducers 284. The error signal circuit 288 compares the desired pressure signal with the actual pressure signal and produces an error, or difference signal, which is fed through the feedback correction circuit 290 to the DC servoamplifiers 264 to provide a correction signal in order to correct the actual pressure to its desired pressure, and thus closely maintain the actual pressure in the simulated left ventricle at the desired level.

While FIG. 6 shows a block diagram of a single system, the actuators and signal circuits such as the DC amplifier 264 and the error signal circuit 288, or subsystems thereof, may be added in order to provide separate circuitry and signal paths, and separate measurements, for each of the plurality of systems including actuators 208, 210, 212 and 214. In order to more closely simulate the action of a human heart by the simulated left ventricle 202, any number of actuators and piston drivers may be provided, along with separate selected input signals for the various actuators. For example, arrhythmias and other disorders of the heart can be closely simulated because of the great flexibility provided through the use of multiple electronic signals, electronic actuators, and electronic feedback. Unlike pneumatic or mechanical systems which have been used in the past for heart actuators or simulators, the present invention is extremely versatile and quiet, enabling a closer approximation or simulation of the environment to which the heart valves 220 and 222 will be, or are, subjected to in in vivo use. Also, the frequency of various signals provided to the electronic system can be readily increased, enabling acceleration of testing of heart valves, which is of considerable significance in, for example, the life testing of simulated actuation of heart valves.

Accordingly, it is to be appreciated that the subject invention provides a very useful tool to more closely simulate the loading and operation of replacement heart valves in vitro. Also, the subject invention varies the pressure applied to a fluid which actuates the heart valve 12 rather than varying the fluid flow or displacement as is accomplished in certain prior art devices. By simply varying the amplitude of the input signal, the applied pressure can be varied in a corresponding manner. Also, by simply varying the current through the coil such as 76, the flow of fluid through the heart valve 12 can also be controlled.

In addition, since the human heart includes a pair of valves, the mitral valve on the input side and the aortic valve on the output side, it is possible to more closely simulate the operation of the human heart by providing two heart valves such as 220 and 222 spaced within the simulated heart or vessel 20 as shown in FIG. 5.

The closed loop system provided by the feedback from the pressure transducer 36 enables the provision of a pressure which very closely automatically maintains the desired pressure. This correction is continuous and can be accomplished for every "heartbeat" of the heart valve 12.

Still further, it is to be noted that there are no moving parts which touch one another to provide friction and introduce errors into the system. The only moving part is the flexible diaphragm 74 with its attached coil 76 which is energized for movement of the coil 76 in the air gap 80, such that there is no touching between, or friction resulting from, moving parts. The diaphragm 74 directly contacts the fluid being pumped. Since there are no moving contacting parts, the present invention is exceedingly quiet which is highly desirable in those cases where the audio or audible operation of the replacement heart valve is being studied and tested.

While the present invention has been described with respect to certain preferred embodiments thereof, it is to be understood that numerous variations in the details of construction, the arrangement and combination of parts, and the type of materials used may be made without departing from the spirit and scope of the invention.

What I claim is:

1. An in vitro tester for fluid valves used as replacements in the human heart comprising:
    means to mount in vitro a human heart replacement valve;
    a fluid source providing a means fluid pressure and fluid flow;
    fluid conductors to connect said fluid source to said heart valve for pulsed actuation of said heart valve; and
    a pressure generator to apply a periodic pulsed pressure to said fluid to cause said pulsed actuation;
    said pressure generator including:
        a diaphragm in contact with said fluid;
        a coil secured to said diaphragm;
        means to generate a first magnetic field about said coil; and
    means to selectively apply a plurality of different types of signals to cause current flow through said coil of said pressure generator;
    said current flow generating an electromagnetic field which interacts with said first magnetic field to move said diaphragm against said fluid to provide pressure pulses to said fluid in response to said current flow causing actuation of said heart valve responsive to said current flow;
    whereby variable control of actuation of said human heart replacement valves can be provided in vitro to more closely simulate various heart pumping actions, including abnormal conditions and accelerated pumping action.

2. The replacement heart valve tester of claim 1 wherein said means to apply a plurality of different types of signals is a variable frequency signal generator to selectively provide signals having a frequency much higher than the frequency of the normal heartbeat of the human heart in order to accelerate the testing of said heart valve.

3. The replacement heart valve tester of claim 2 wherein said pressure generator provides a signal selected from the group consisting of square wave, pulsed, sinusoidal, or random signals.

4. The replacement heart valve tester of claim 1 wherein a plurality of pressure generators are provided in contact with said fluid.

5. The replacement heart valve tester of claim 4 further including means for applying signals of differing phases to different ones of said pressure generators to simulate an arrhythmia in a heartbeat.

6. The replacement heart valve tester of claim 5 wherein said signals of differing phases are provided by one or more phase shifting means.

7. The replacement heart valve tester of claim 3 further including means for selectively applying a DC offset to said signal.

8. The replacement heart valve tester of claim 3 wherein said means to mount includes a sewing ring of the type used in said human heart replacement valves.

9. The replacement heart valve tester of claim 8 wherein said sewing ring is DACRON fabric.

10. The replacement heart valve tester of claim 2 wherein a counter means is provided to measure the number of higher frequency signals to which said valve is subjected.

11. The replacement heart valve tester of claim 1 wherein a detector means is provided to monitor operation, and to detect irregularities in the operation of said valve.

12. The replacement heart valve tester of claim 11 wherein said detector means includes an audio tester to monitor the audio characteristics of the operation of said valve.

13. The replacement heart valve tester of claim 1 wherein said means to apply a plurality of different types of signals includes a recorded signal derived from an actual human heart.

14. The replacement heart valve tester of claim 13 wherein said recorded signal derived from an actual human heart is a recorded signal provided by a catheter in a human, the heart signal of whom is recorded.

15. The replacement heart valve tester of claim 14 wherein said recorded signal is provided at an increased speed to enable acceleration of the testing.

16. The replacement heart valve tester of claim 1 wherein said means to generate a first magnetic field is a permanent magnet positioned around said coil and forming a narrow airgap between said magnet and said coil.

17. The replacement heart valve tester of claim 4 wherein a plurality of pressure generators are provided, with at least one pressure generator positioned on each opposite side of said valve.

18. The replacement heart valve tester of claim 1 wherein a variable pump and valve are provided to control the mean fluid pressure and fluid flow provided by said fluid source.

19. The replacement heart valve tester of claim 18 wherein the movement of said diaphragm superimposes a variable fluid pressure and fluid flow on said mean fluid pressure and fluid flow.

20. A method of in vitro testing replacement heart valves of the type implanted in the human heart comprising:
   mounting said replacement heart valve in a fluid;
   said fluid having a mean fluid pressure and flow;
   providing a heart valve actuator including a flexible diaphragm in contact with said fluid, and a coil assembly connected to said diaphragm and magnetically coupled to an associated magnet field;
   periodically energizing said coil with an electrical pulsed signal selected from the group consisting of sinusoidal, triangular, square and random electrical pulses, and a recording of an actual human heart to cause said coil and diaphragm to move in said magnetic field;
   movement of said diaphragm applying pressure to said fluid and against said replacement heart valve to actuate said replacement heart valve in response to said signal;
   recording the response of said replacement heart valve to said electrical signal to provide a response database which includes responses of said replacement heart valve in advance of irregularities occurring in said heart valve;
   monitoring the heart action of a person having an implanted heart valve to provide implanted heart performance data; and
   comparing said implanted heart performance data and said response database to detect similarities which may indicate potential irregularities in said implanted heart valve.

21. The method of testing replacement heart valves of claim 20 wherein a plurality of heart valve actuators are provided having their diaphragms in contact with said fluid, and the additional step of providing a selected electrical pulsed signal to each of said heart valve actuators.

22. The method of testing replacement heart valves of claim 21 wherein the selected signals provided to said valve actuators are provided with a phase displacement between the signals to simulate abnormalities in a human heart.

23. The method of testing replacement heart valves of claim 22 including the additional steps of including said fluid in a closed fluid system, and controlling the mean pressure and flow of said fluid within said closed fluid system through said replacement heart valve, with said selected signals actuating said heart valve actuators to superimpose a pulsed pressure and flow onto said mean pressure and flow such that said flow has a degree of cavitation.

24. The method of testing replacement heart valves of claim 23 wherein said mean pressure and flow and said selected signals are adjusted to simulate actuation of said replacement heart valve in a controlled manner, and the additional step of varying the degree of cavitation in the flow of said fluid through said replacement heart valve.

25. The method of testing replacement heart valves of claim 24 including the additional step of comparing the operation and life of said replacement heart valve under various conditions of cavitation in the flow.

26. The method of testing replacement heart valves of claim 25 including the additional step of testing various designs of replacement heart valves including variations in material to determine the ability of such various designs to withstand such cavitation.

27. The method of testing replacement heart valves of claim 20 wherein said recording includes audio recording of the operation of said replacement heart valves.

28. The method of testing replacement heart valves in claim 27 wherein said monitoring includes audio monitoring of said implanted heart valve.

29. The method of testing replacement heart valves in claim 28 including the additional step of compiling a monitored database of the heart action of persons having implanted heart valves in order to detect potential irregularities, and to detect differences in subsequent monitoring.

30. A method of testing replacement heart valves of the type implanted in a human heart comprising:
   mounting said replacement heart valve in a fluid;
   said fluid having a mean fluid pressure and flow;
   providing a heart valve actuator including a flexible diaphragm in contact with said fluid, and a coil assembly positioned in a magnetic field and connected to said diaphragm;
   monitoring the heart action of a person having an implanted heart valve to provide an implanted heart valve signal;
   energizing said coil with said implanted heart signal to move said coil in said magnetic field to apply pressure to said fluid through said diaphragm to move said fluid against said replacement heart valve and actuate said replacement valve in response to said implanted heart valve signal; and
   increasing the frequency of said implanted heart signal to accelerate the actuation of said replacement heart valve to determine if any irregularities in said replacement heart valve occur which may indicate possible future irregularities in said implanted heart valve in response to said heart action of said person.

31. The method of testing replacement heart valves in claim 30 wherein said monitoring of heart action includes audio monitoring of said implanted heart valve.

32. The method of testing replacement heart valves of claim 31 wherein a plurality of heart valve actuators are provided having their diaphragms in contact with said fluid, and the additional step of providing a selected signal to each of said heart valve actuators.

33. The method of testing replacement heart valves of claim 32 wherein the selected signals provided to each of said heart valve actuators are phase displaced to simulate the actuation of said replacement heart valve when implanted in a human heart.

34. The method of testing replacement heart valves of claim 33 wherein an adjustable pump and flow control are provided to adjust the mean fluid pressure and flow of said fluid.

35. A method of testing replacement heart valves of the type implanted in the human heart comprising:
   mounting a first replacement heart valve in a fluid;
   providing a heart valve actuator including a flexible diaphragm in contact with said fluid, and a coil assembly physically connected to said diaphragm and magnetically coupled to an associated magnet field;
   monitoring the heart action of a person in need of an implanted heart valve to provide an actual heart signal;

energizing said coil with said actual heart signal to move said coil in said magnetic field to apply pressure to said fluid through said diaphragm to move said fluid against said first replacement heart valve in response to said actual heart signal;

accelerating the actuation of said first replacement heart valve by increasing the speed of said actual heart signal to determine if any irregularities in said replacement heart valve occur which may indicate possible future irregularities in response to said heart action of said person; and substituting one or more additional replacement heart valves in place of said first replacement heart valve to compare the suitability of each of the various heart valves as an actual heart valve replacement for said person.

* * * * *